(12) United States Patent
Rooney et al.

(10) Patent No.: US 9,439,686 B2
(45) Date of Patent: Sep. 13, 2016

(54) SPINAL CORRECTION SYSTEM AND METHOD

(71) Applicant: Warsaw Orthopedic, Inc., Warsaw, IN (US)

(72) Inventors: Richard Rooney, Medina, WA (US); William Alan Rezach, Atoka, TN (US); Joshua W. Simpson, Collierville, TN (US); Sean P. Skubitz, Forest Lake, MN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 347 days.

(21) Appl. No.: 13/838,846

(22) Filed: Mar. 15, 2013

(65) Prior Publication Data

US 2014/0277149 A1   Sep. 18, 2014

(51) Int. Cl.
*A61B 17/70* (2006.01)
*A61B 17/84* (2006.01)

(52) U.S. Cl.
CPC .......... *A61B 17/7053* (2013.01); *A61B 17/842* (2013.01)

(58) Field of Classification Search
CPC ............ A61B 17/7053; A61B 17/885; A61B 17/8866; A61B 17/8869
USPC ................. 606/263, 103, 74, 139, 224, 225
See application file for complete search history.

(56) References Cited

U.S. PATENT DOCUMENTS

| | | | | |
|---|---|---|---|---|
| 5,307,790 A | * | 5/1994 | Byrne | A61B 17/02 24/20 R |
| 5,549,619 A | * | 8/1996 | Peters | A61B 17/0401 606/151 |
| 5,683,404 A | * | 11/1997 | Johnson | 606/151 |
| 5,766,218 A | * | 6/1998 | Arnott | A61B 17/823 24/16 PB |
| 6,086,590 A | * | 7/2000 | Margulies et al. | 606/263 |
| 7,184,842 B2 | | 2/2007 | Siefert et al. | |
| 7,212,864 B2 | | 5/2007 | Wahlstrand et al. | |
| 2003/0023241 A1 | * | 1/2003 | Drewry et al. | 606/61 |
| 2005/0288674 A1 | * | 12/2005 | Golobek | A61B 17/82 606/74 |
| 2010/0274289 A1 | * | 10/2010 | Carls | A61B 17/842 606/263 |
| 2012/0041441 A1 | * | 2/2012 | Bernstein et al. | 606/74 |

FOREIGN PATENT DOCUMENTS

EP    2725993    7/2014

* cited by examiner

*Primary Examiner* — Ellen C Hammond
*Assistant Examiner* — Christina Negrellirodrigue

(57) ABSTRACT

A spinal construct comprises a pliable lead. A longitudinal member is flexible relative to the lead. The longitudinal member extends between a first end connected to the lead and a second end defining an opening configured for movement of the lead therethrough and disposal of the longitudinal member such that the longitudinal member is disposed about spinal tissue. Systems and methods are disclosed.

16 Claims, 12 Drawing Sheets

US 9,439,686 B2

SPINAL CORRECTION SYSTEM AND METHOD

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, bone screws and sub-laminar wire, for stabilization of a treated section of a spine. This disclosure describes an improvement over these prior art technologies.

SUMMARY

In one embodiment, a spinal construct is provided. The spinal construct comprises a pliable lead. A longitudinal member is flexible relative to the lead. The longitudinal member extends between a first end connected to the lead and a second end defining an opening configured for movement of the lead therethrough and disposal of the longitudinal member such that the longitudinal member is disposed about spinal tissue. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
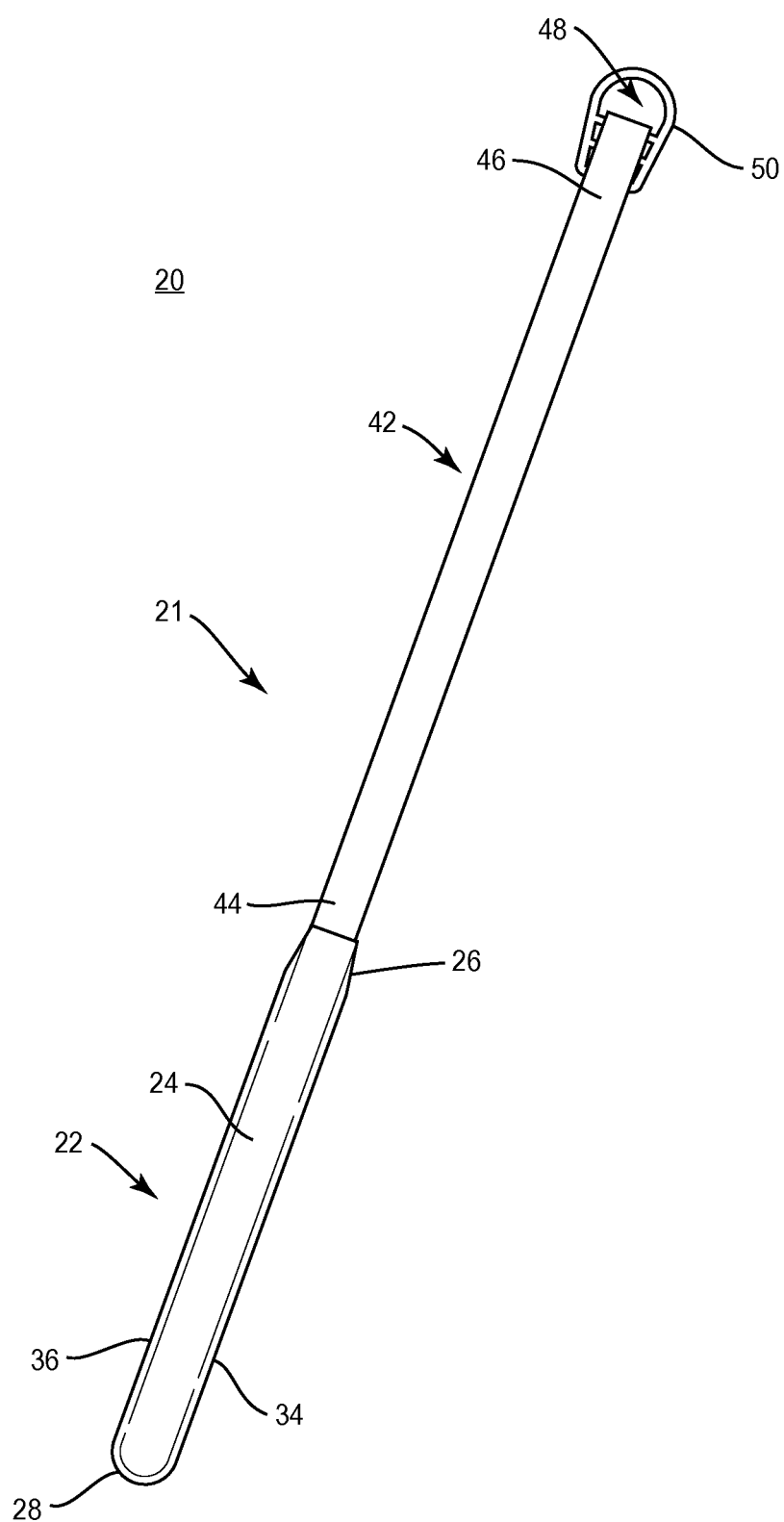
FIG. 1 is a plan view of components of one embodiment of a spinal correction system in accordance with the principles of the present disclosure.

The exemplary embodiments of a surgical system and related methods of use are discussed in terms of medical devices for the treatment of musculoskeletal disorders and more particularly, in terms of a spinal correction system. In some embodiments, the spinal correction system may be employed in applications for correction of deformities, such as scoliosis and kyphosis.

In one embodiment, the spinal correction system includes a spinal construct comprising a tether used for passing under the lamina and above the dura of the spinal cord. In some embodiments, an end or lead of the spinal construct is paddle-shaped. In some embodiments, the paddle-shaped lead provides a safe, blunt end that aids in passing the tether under the lamina and above the dura. In one embodiment, the lead is made of silicone. In some embodiments, the silicone used is sufficiently rigid so that the spinal construct can be passed under the lamina and above the dura. In some embodiments, the silicone used is also sufficiently slick so that the spinal construct does not stick to the dura or the underside of the lamina during passing. These features provide, for example, an increase in safety and an increase in the speed that a spinal construct can be passed under the lamina. In one embodiment, the tether is made of, for example, polyester, polyethylene glycol, or a material having similar properties and the lead is made of silicone.

In one embodiment, the spinal correction system includes a spinal construct comprising a lead molded onto an end of a tether that allows for its passage under a lamina without adhering to a dura. In one embodiment, the lead is made of a low friction material that allows for its passage under the lamina without adhering to the dura. In one embodiment, the lead is made of a pliable material that allows for passage without harming any of the sensitive spinal anatomy. In one embodiment, the lead is made of a soft and flexible material. In one embodiment, at least a portion of the spinal construct is opaque to allow for visualization in situ. In one embodiment, at least a portion of the spinal construct is radiolucent with addition of barium sulfate into molding.

In one embodiment, the spinal correction system includes a spinal construct comprising a lead having a fully rounded tip to protect a spinal anatomy. In one embodiment, the lead is approximately 40 millimeters (mm) to 60 mm in length.

In one embodiment, the lead is approximately 6 mm in width. In one embodiment, the lead is approximately 2 mm thick.

In one embodiment, the lead has an arcuate configuration with an approximate bend radius in a range of 20 mm to 100 mm. In some embodiments, the range of the bend radius of the lead can be different for each region of the spine. For example, in the thoracic region of the spine, the lead can have a radius of curvature of 80 mm. For example, in the thoracic region of the spine, the lead having a radius of curvature of 80 mm is fabricated from a soft and flexible material. For example, in the lumbar or thoracic region of the spine, the lead can have a radius of curvature of 30 mm. In some embodiments, the lead is curved to allow for its passage under the lamina. In some embodiments, the bend radius of the lead is configured to allow for its passage without sticking to the dura and for a surgeon to grasp the tip of the lead with surgical instruments to pull the tether out of a sub-laminar cavity.

In one embodiment, the spinal correction system includes a spinal construct employed with a method that includes the steps of: placing a tether of the spinal construct using surgical instruments such that a silicone end of a lead of the spinal construct provides safety in passing under a lamina; grasping an end of the tether and pulling the tether under the lamina; passing the end of the tether through a loop attached to the tether; pulling the silicone end through the loop; and cinching the tether to the anatomy.

In some embodiments, the lead can have a linear configuration. In some embodiments, the lead can have a curvature to facilitate grabbing the lead with a forceps instrument such that the curved lead can pass under the lamina and lift away from the dura. In some embodiments, the lead is made of a pliable and/or soft and flexible material having a durometer of between 30 A and 60 A.

In one embodiment, the tether has a second end opposite the lead end having a loop configured for disposal of the tether. In one embodiment, the loop is monolithically formed with the tether and comprises the same material as the tether, such as, for example, a fabric loop. In one embodiment, the loop is fabricated from an implantable material and attached to the tether, such as, for example, a buckle tied to the tether. In one embodiment, the buckle is crimped onto the tether.

In some embodiments, one or all of the components of the spinal correction system may be disposable, peel-pack, pre-packed sterile devices. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
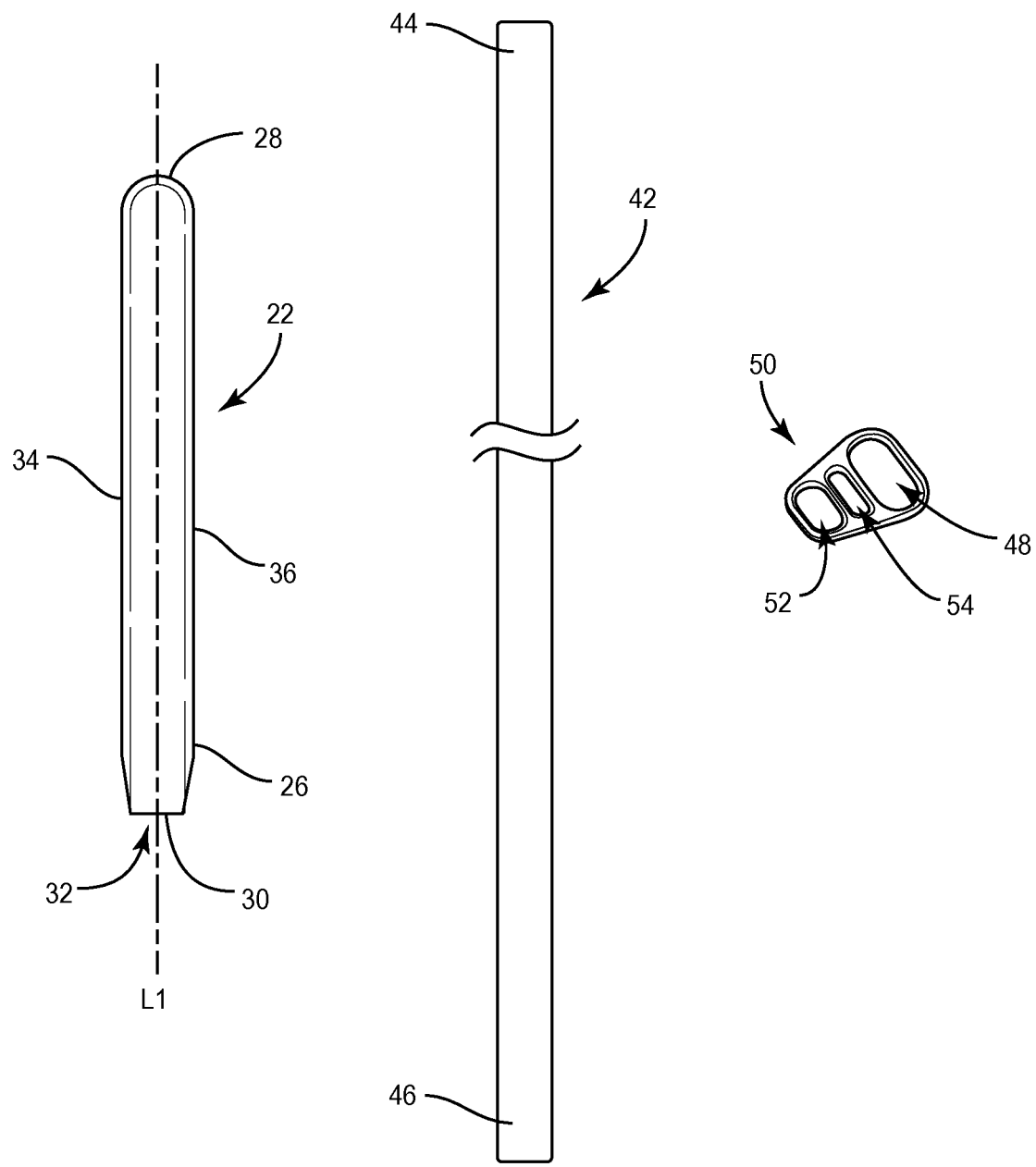
FIG. 2 is a plan view of the components shown in FIG. 1 with parts separated.
Figure 3:
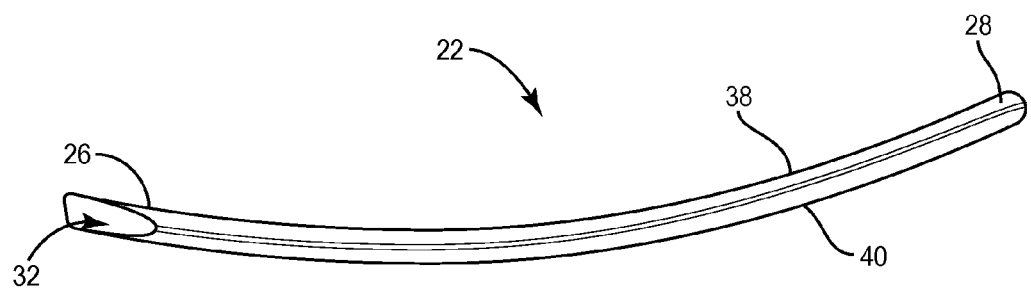
FIG. 3 is a side view of a component shown in FIG. 1.

The following discussion includes a description of a spinal correction system, related components and methods of employing the surgical correction system in accordance with the principles of the present disclosure. Alternate embodiments are also disclosed. Reference will now be made in detail to the exemplary embodiments of the present disclosure, which are illustrated in the accompanying figures. Turning to FIGS. 1-3, there are illustrated components of a spinal correction system 20.

The components of spinal correction system 20 can be fabricated from biologically acceptable materials suitable for medical applications, including metals, synthetic polymers, ceramics, bone material, tissue and/or their composites, depending on the particular application and/or preference of a medical practitioner. For example, the components of spinal correction system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal correction system 20 may have material composites, including the above materials, to achieve various desired characteristics such as strength, rigidity, elasticity, compliance, biomechanical performance, durability and radiolucency or imaging preference. The components of spinal correction system 20, individually or collectively, may also be fabricated from a heterogeneous material such as a combination of two or more of the above-described materials. The components of spinal correction system 20 may be monolithically formed, integrally connected or include fastening elements and/or instruments, as described herein.

Spinal correction system 20 is employed, for example, with an open, mini-open or minimally invasive including percutaneous surgical technique to attach a spinal rod to a spine that has a spinal disorder. In one embodiment, the spinal rod may be affixed to a selected section of the spine and/or other anatomy while allowing for growth and adjustments to a concave side of a plurality of vertebrae for a correction treatment to treat various spine pathologies, such as, for example, adolescent idiopathic scoliosis and Scheuermann's kyphosis.

Spinal correction system 20 includes a spinal construct 21. Spinal construct 21 includes a lead 22 having a pliable configuration such that lead 22 can be passed and/or guided through cavities of spinal tissue to resist and/or prevent non-desirable and/or harmful engagement with selected and/or sensitive anatomy of the spinal tissue. In some embodiments, lead 22 is configured for manipulation with a surgical instrument. In some embodiments, lead 22 is soft and flexible and configured to pass through a sub-laminar cavity of vertebrae without adhering to dura matter of a spinal cord and/or surfaces of a lamina of a vertebral level. In some embodiments, all or only a portion of lead 22 is fabricated from a pliable, low-friction material, such as, for example, silicone, polyurethane, silicone-polyurethane copolymers, polymeric rubbers, polyolefin rubbers, elastomers, rubbers, thermoplastic elastomers, thermoset elastomers and elastomeric composites. In some embodiments, all or only a portion of lead 22 is fabricated from a semi-rigid, rigid or elastic configuration, relative to other components of spinal construct 21 and/or have elastic properties, such as the elastic properties corresponding to the material examples described above. In some embodiments, all or only a portion of lead 22 is fabricated from a material having a durometer in the range of approximately 30 A to 60 A under the ASTM D2240 type A scale. In one embodiment, lead 22 comprises silicone having a durometer of 30 A to 60 A.

Lead 22 includes an outer surface 24 having an average surface roughness such that lead 22 can be passed through the cavities of the spinal tissue and resist and/or prevent non-desirable and/or harmful adherence with selected and/or sensitive anatomy of the spinal tissue, for example, a lamina of a vertebral level and/or the dura matter. In some embodiments, all or only a portion of surface 24 has an average surface roughness in a range of approximately 4 to 32 micro inches. In some embodiments, all or only a portion of surface 24 has an average surface roughness in a range of approximately 4 to 16 micro inches. In some embodiments, all or only a portion of surface 24 contacts spinal tissue, such as, for example, a lamina of a vertebral level and/or dura matter of a spinal cord, and the coefficient of kinetic friction of surface 24 is in a range of approximately 0.04-0.50, such that surface 24 slides along selected and/or sensitive anatomy of the spinal tissue with minimal resistance, adherence and/or sticking to the lamina and/or dura matter.

Lead 22 extends between a proximal end 26 and a distal end 28 defining a length of lead 22 therebetween. In some embodiments, lead 22 has a length of approximately 40 mm to 60 mm so that lead 22 can be passed under lamina of a particular vertebral level. Lead 22 defines a longitudinal axis L1. End 28 has a tip including a blunt shape to resist and/or prevent non-desirable and/or harmful engagement with selected and/or sensitive anatomy of the spinal tissue. In some embodiments, end 28 has an arcuate configuration. In some embodiments, end 28 can have various shape configurations, such as, for example, oval, oblong, polygonal, irregular, uniform, non-uniform, variable and/or tapered.

The body of lead 22 includes a paddle configuration. In one embodiment, lead 22 includes a paddle configuration having a substantially uniform thickness. In some embodiments, lead 22 is variously shaped, such as, for example, oval, oblong, triangular, square, polygonal, irregular, uniform, non-uniform, offset, staggered, undulating, arcuate, variable and/or tapered. In some embodiments, lead 22 may have various cross section configurations, such as, for example, oval, oblong, triangular, rectangular, square, polygonal, irregular, uniform, non-uniform, variable, tubular and/or tapered.

Lead 22 includes an inner surface 30 defining a cavity 32 configured for disposal of a longitudinal member, such as, for example, a tether 42. In one embodiment, surface 30 is permanently molded with tether 42. In some embodiments, surface 30 is detachably or removably engaged with tether 42. In some embodiments, surface 30 can be variously connected with tether 42, such as, for example, monolithic, integral connection, frictional engagement, threaded engagement, mutual grooves, screws, adhesive, nails, barbs and/or raised element. In some embodiments, cavity 32 can have various cross section configurations, such as, for example, those alternatives described herein.

Lead 22 includes sides 34, 36 extending in a substantially parallel orientation. Sides 34, 36 define a uniform width of lead 22. In one embodiment, lead 22 has a width of approximately 6 mm. In some embodiments, sides 34, 36 may be disposed at alternate orientations, such as, for example, transverse, perpendicular and/or other angular orientations such as acute or obtuse, co-axial and/or may be offset or staggered.

Lead 22 includes a surface 38 defining a substantially even face and being oriented in a first direction and a surface 40 defining a substantially even face and being oriented in a second direction opposite the first direction. Surfaces 38, 40 define a thickness of lead 22. Lead 22 has a substantially uniform thickness along its length. In some embodiments, the thickness of lead 22 may be non-uniform, uniformly increasing or uniformly decreasing. In some embodiments, lead 22 has a thickness of approximately 2 mm. Surface 38 is concavely curved and surface 40 is convexly curved such that lead 22 is arcuate along its length between ends 26, 28. Lead 22 has an arcuate configuration having a radius of curvature. In some embodiments, lead 22 has a radius of curvature in a range of approximately 20 mm to 100 mm. In one embodiment, surface 38 is oriented parallel with surface 40.

Spinal construct 21 includes tether 42, which is substantially flexible relative to lead 22. Tether 42 is a flexible longitudinal element that extends between an end 44 and an end 46. End 44 is connected to lead 22 and disposed with cavity 32, as described herein.

End 46 is connected to a loop, described herein, which defines an opening that is configured for disposal of a portion of tether 42. The loop supports tether 42 such that tether 42 can be adjustably tensioned about a targeted portion of an anatomy of a body for attachment of tether 42 with the targeted portion of the anatomy, such as, for example, a lamina of a vertebra, as described herein. In some embodiments, lead 22 and/or tether 42 may be manipulated manually and/or with a surgical tensioning instrument, such as, for example, a forceps. In some embodiments, the targeted portion of the vertebra may include a lamina, transverse process and/or pedicle regions of a vertebral level. In some embodiments, spinal correction system 20 may include one or a plurality of spinal constructs 21, each spinal construct 21 being configured for disposal about a single and separate vertebral level. In some embodiments, a single vertebral level may include one or a plurality of spinal constructs 21. In some embodiments, spinal construct 21 may include one or a plurality of tethers 42 disposed about a single vertebral level.

Tether 42 has a flexible configuration and may be fabricated from materials, such as, for example, polyester, polyethylene, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of tether 42 includes movement in a lateral or side to side direction and prevents expanding and/or extension in an axial direction upon tensioning of tether 42 and attachment with a targeted portion of the vertebra. In some embodiments, all or only a portion of tether 42 may have a semi-rigid, rigid or elastic configuration, and/or have elastic properties, such as the elastic properties corresponding to the material examples described above. In some embodiments, tether 42 may be compressible in an axial direction.

Tether 42 can have a uniform thickness/diameter. In some embodiments, tether 42 may have various surface configurations, such as, for example, smooth and/or surface configurations to enhance fixation, such as, for example, rough, arcuate, undulating, porous, semi-porous, dimpled, polished and/or textured according to the requirements of a particular application. In some embodiments, the thickness defined by tether 42 may be uniformly increasing or decreasing, or have alternate diameter dimensions along its length. In some embodiments, tether 42 may have various cross section configurations, such as, for example, oval, oblong, triangular, rectangular, square, polygonal, irregular, uniform, non-uniform, variable and/or tapered. In some embodiments, the surface of tether 42 may include engaging structures, such as, for example, barbs, raised elements and/or spikes to facilitate engagement with tissue of the targeted vertebral level.

In some embodiments, tether 42 may have various lengths. In some embodiments, tether 42 may be braided, such as a rope, or include a plurality elongated elements to provide a predetermined force resistance. In some embodiments, tether 42 may be made from autograft and/or allograft, and be configured for resorbable or degradable applications.

End 46 of tether 42 is connected to a loop, such as, for example, a buckle 50. Buckle 50 defines an opening 48 configured for movement of lead 22 therethrough and disposal of tether 42 such that tether 42 is disposable about spinal tissue, such as, for example, the lamina of a vertebral level. Buckle 50 is separate and attachable with tether 42.

Buckle 50 includes an inner surface that defines a plurality of openings, which include apertures 52, 54 configured for threaded connection and securement of end 46 with buckle 50 such that end 46 includes opening 48. End 46 is disposed with apertures 52, 54 such that tether 42 is affixed with buckle 50. Tether 42 is adjustable with opening 48 to tension tether 42 about spinal tissue, for example, a lamina of a vertebral level, to fix spinal construct 21 with the vertebral level.

Figure 4:
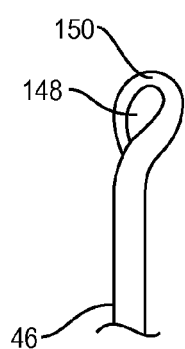
FIG. 4 is a break away plan view of a component of one embodiment of a spinal correction system in accordance with the principles of the present disclosure.
Figure 5:
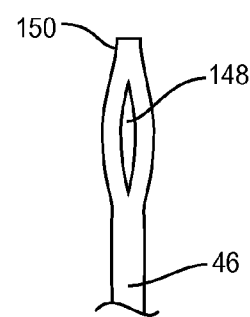
FIG. 5 is a break away plan view of a component of one embodiment of a spinal correction system in accordance with the principles of the present disclosure.

In one embodiment, as shown in FIG. 4, spinal construct 21 includes an end 46 comprising a loop 150 having an inner surface that defines an opening 148 configured for movement of lead 22 therethrough and disposal of tether 42 such that tether 42 is disposable about spinal tissue, such as, for example, the lamina of a vertebral level. Loop 150 is monolithically formed with end 46 and crimped to form opening 148. In one embodiment, as shown in FIG. 5, spinal construct 21 includes an end 46 comprising a loop 250 having an inner surface that defines an opening 248 configured for movement of lead 22 therethrough and disposal of tether 42 such that tether 42 is disposable about spinal tissue, such as, for example, the lamina of a vertebral level. Loop 250 comprises a split configuration of the tether material of end 46 to form opening 248.

In operation, a practitioner manipulates spinal construct 21 for disposal about a vertebral level to fix and/or attach tether 42 with a targeted section of a spine. The targeted section of the spine can include a transverse process and/or a lamina of a vertebral level such that tether 42 connects an implant, such as, for example, a connector and/or a spinal rod with the vertebral level.

Figure 6:
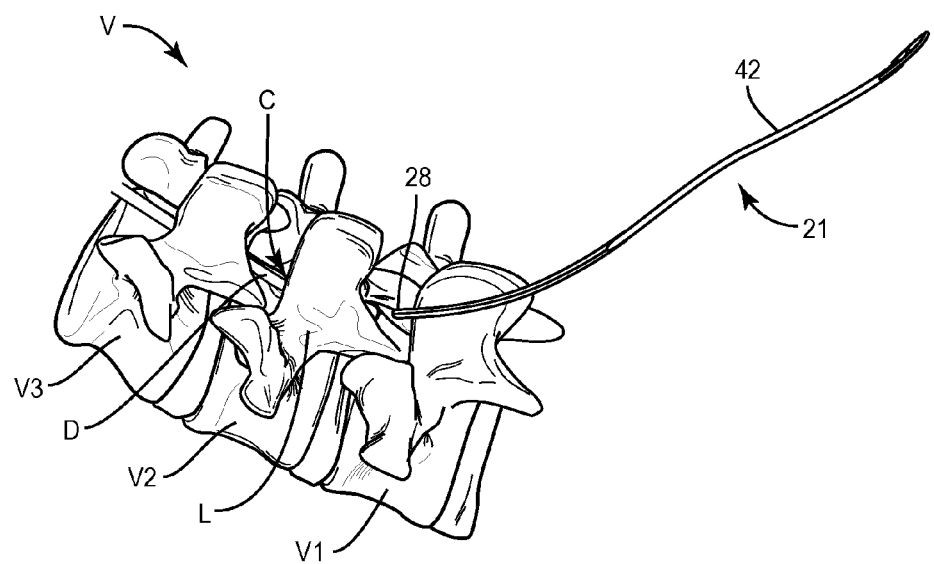
FIG. 6 is a perspective view of components of one embodiment of a spinal correction system in accordance with the principles of the present disclosure disposed with vertebrae.
Figure 7:
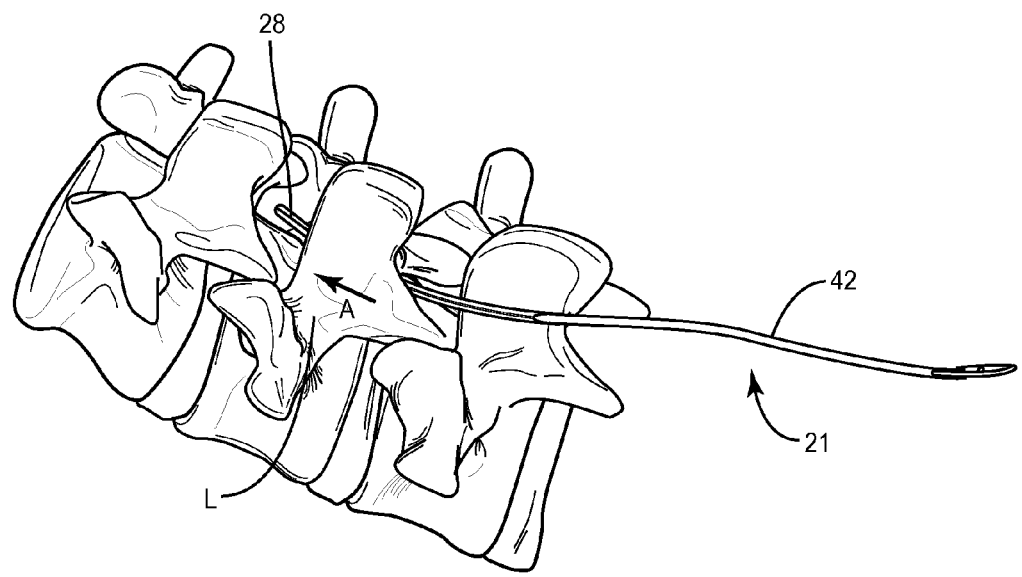
FIG. 7 is a perspective view of the components and vertebrae shown in FIG. 6.
Figure 8:
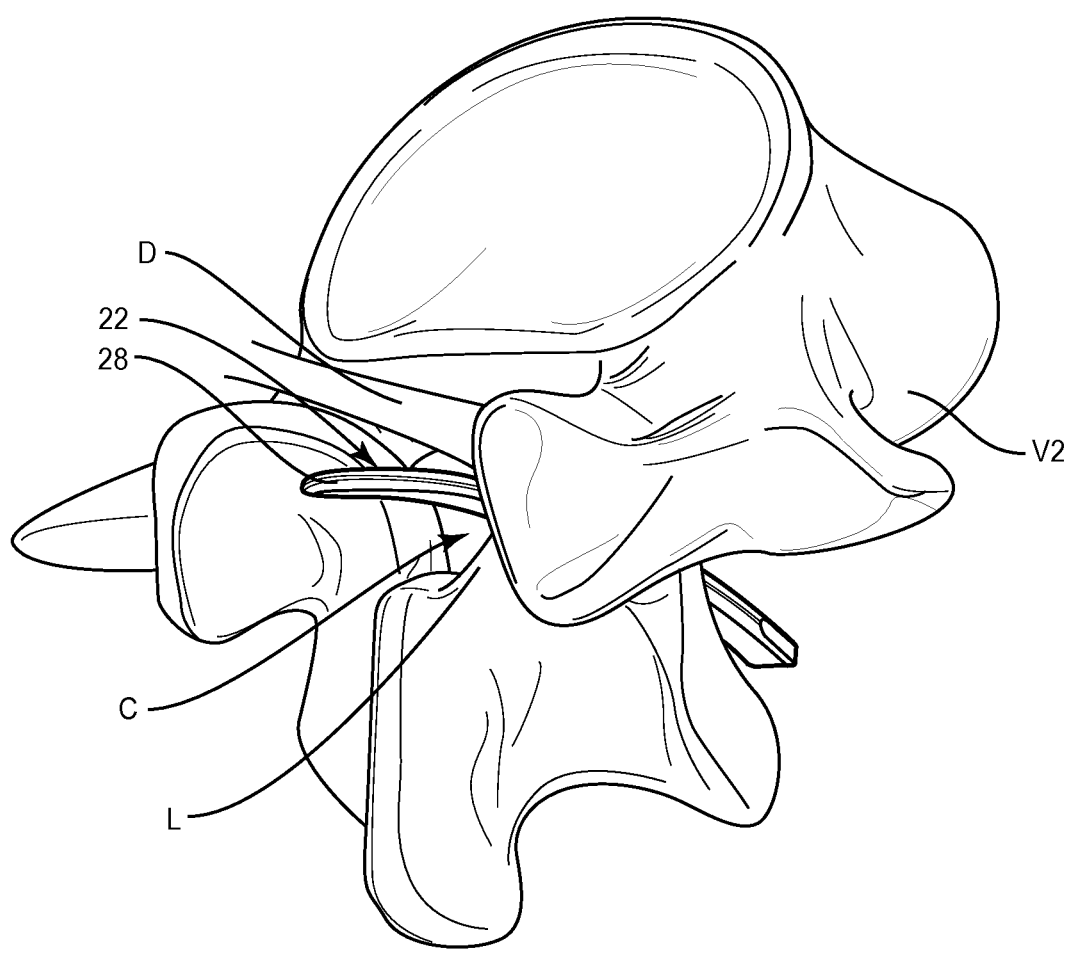
FIG. 8 is a perspective view of the components and vertebrae shown in FIG. 6.

Lead 22 is oriented over the bony anatomy of a vertebra V1, as shown in FIG. 6, and end 28 is aligned for disposal with a sub-laminar cavity C of a vertebra V2. Lead 22 is guided through cavity C, in the direction shown by arrow A in FIG. 7, and passed through cavity C to resist and/or prevent non-desirable and/or harmful engagement with selected and/or sensitive anatomy of the spinal tissue, for example, a lamina L of vertebra V2 and/or dura matter D of a spinal cord and/or other tissue, as shown in FIG. 8. Lead 22 is pliable and configured to pass through cavity C without adhering to dura matter D and/or surfaces of lamina L.

Figure 9:
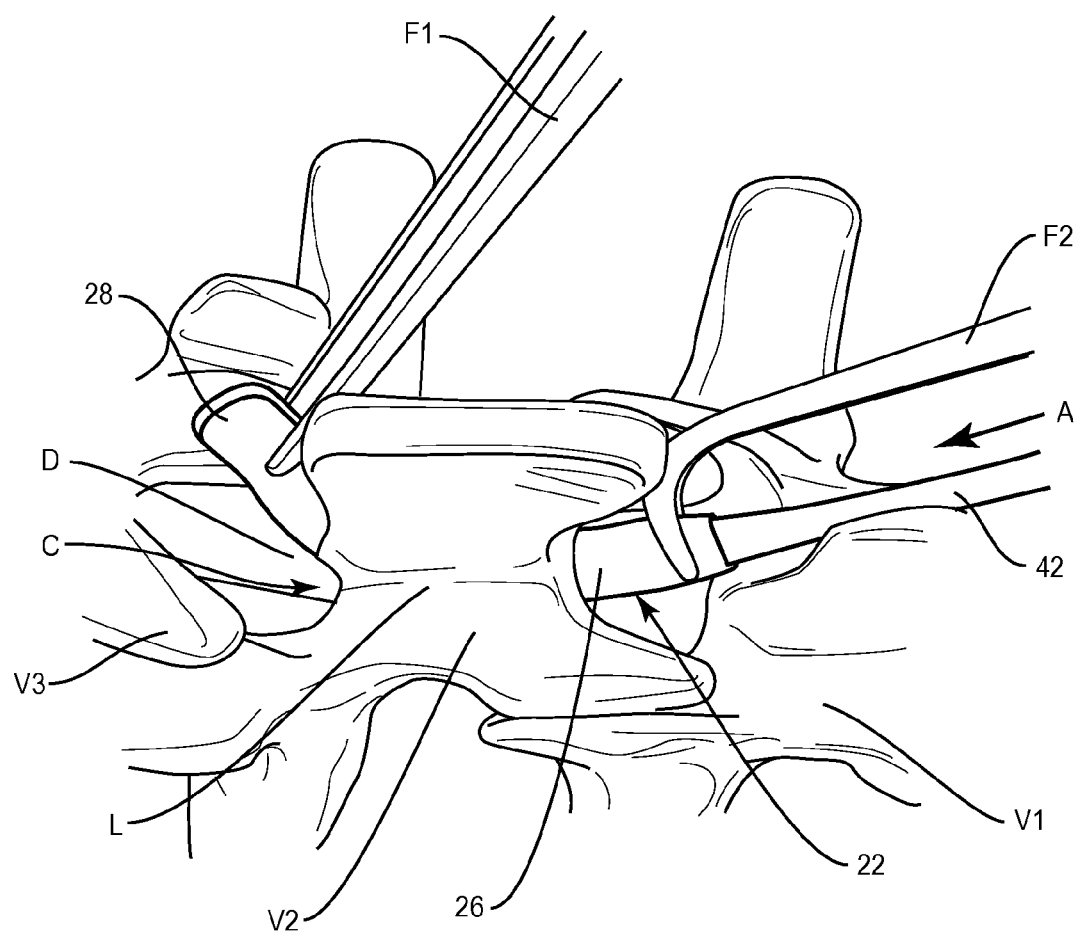
FIG. 9 is a perspective view of the components and vertebrae shown in FIG. 6.
Figure 10:
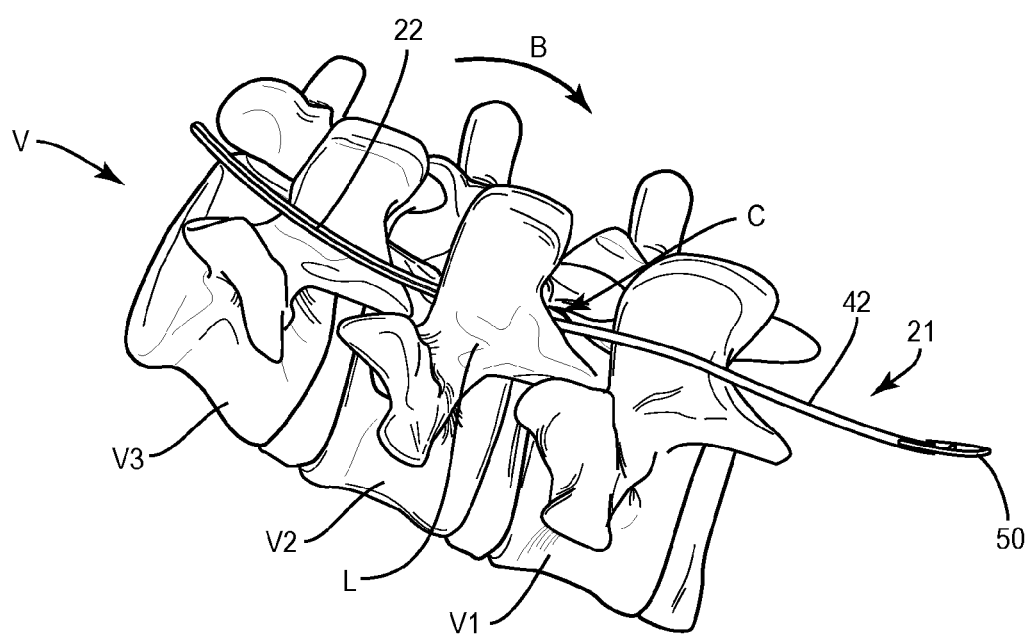
FIG. 10 is a perspective view of the components and vertebrae shown in FIG. 6.

End 28 is grasped with a surgical instrument, such as, for example, a forceps F1 and end 26 is grasped with a surgical instrument, such as, for example, a forceps F2, as shown in FIG. 9. Lead 22 is passed under lamina L, as shown by arrow A, and out of cavity C, in the direction shown by arrow B in FIG. 10, such that the curvature of lead 22 facilitates lead 22 being drawn away from dura matter D to resist and/or prevent non-desirable and/or harmful engagement.

Figure 11:
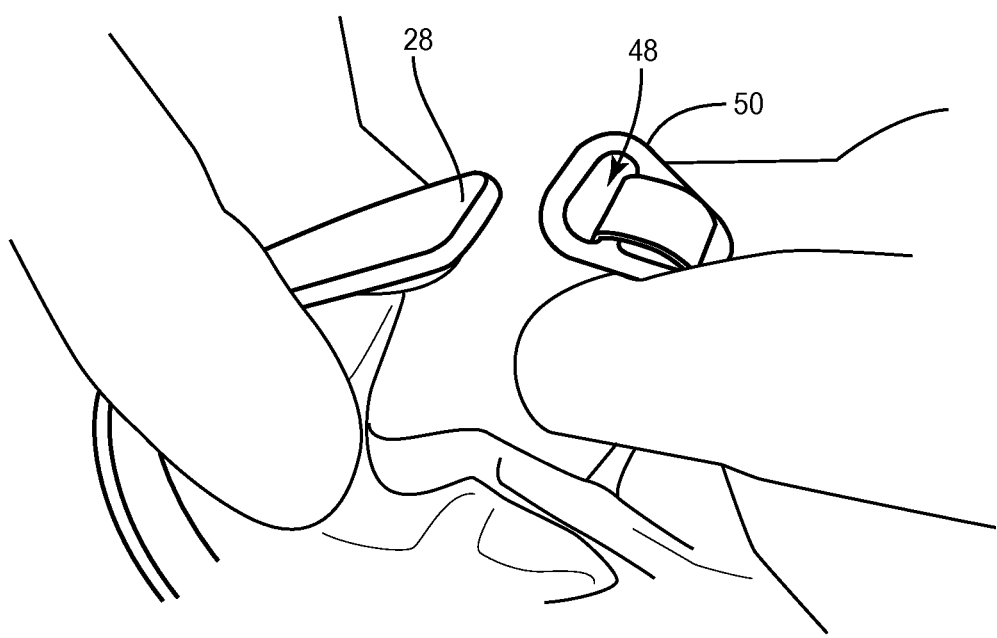
FIG. 11 is a perspective view of the components and vertebrae shown in FIG. 6.
Figure 12:
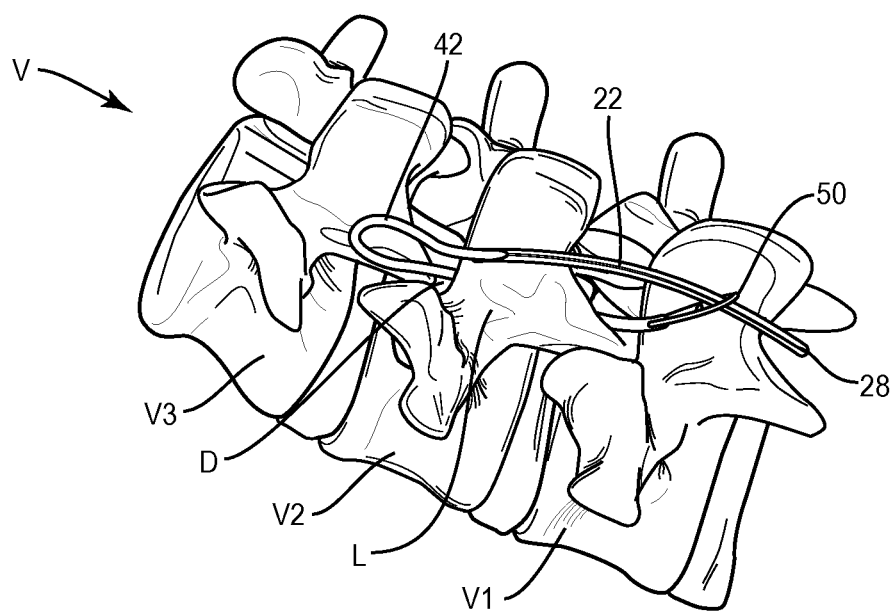
FIG. 12 is a perspective view of the components and vertebrae shown in FIG. 6.
Figure 13:
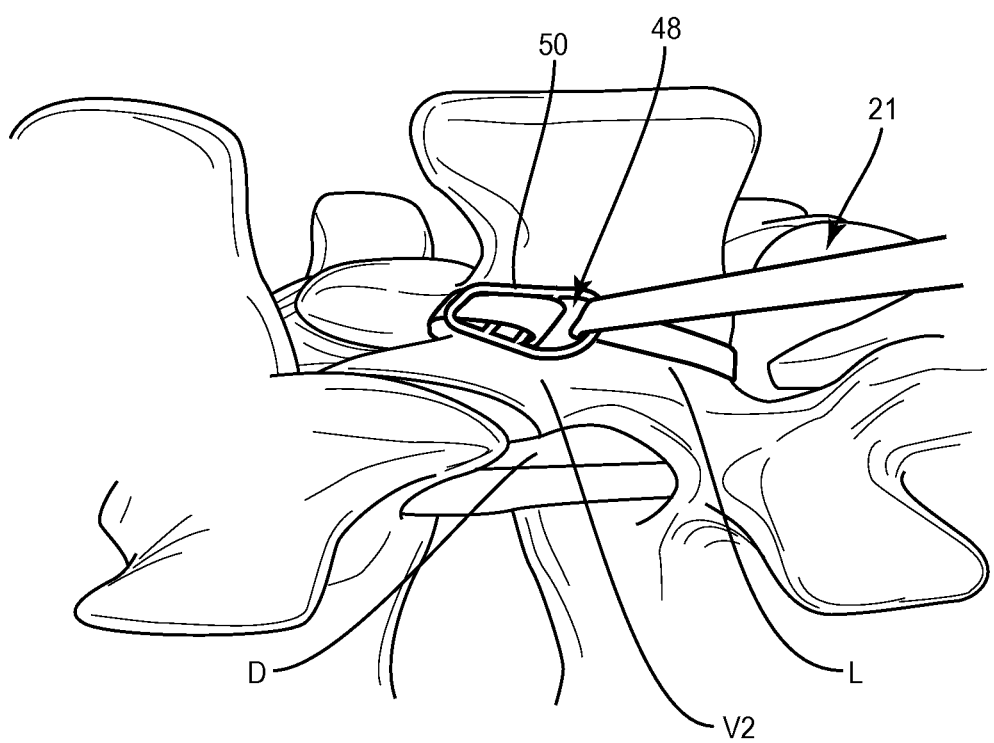
FIG. 13 is a perspective view of the components and vertebrae shown in FIG. 6.

Lead 22 is drawn away from vertebra V2 and tether 42 is disposed about lamina L, as shown in FIGS. 11 and 12. End 28 is passed through opening 48 for tensioning tether 42 with vertebra V2. End 28 is drawn or tensioned to adjustably tighten tether 42 with buckle 50 and to fix tether 42 with lamina L, as shown in FIG. 13.

Spinal correction system 20 includes a spinal rod 58 having a cylindrical cross section configuration. In some embodiments, spinal correction system 20 may include one or a plurality of spinal rods 58, which may be relatively disposed in a side by side, irregular, uniform, non-uniform, offset and/or staggered orientation or arrangement. In some embodiments, spinal rod 58 can have a uniform thickness/diameter. In some embodiments, spinal rod 58 may have various surface configurations, such as, for example, rough, threaded for connection with surgical instruments, arcuate, undulating, dimpled, polished and/or textured according to the requirements of a particular application. In some embodiments, the thickness defined by spinal rod 58 may be uniformly increasing or decreasing, or have alternate diameter dimensions along its length. In some embodiments, spinal rod 58 may have various cross section configurations, such as, for example, oval, oblong, triangular, rectangular, square, polygonal, irregular, uniform, non-uniform, variable and/or tapered. In some embodiments, spinal rod 58 may have various lengths.

Spinal correction system 20 includes an implant connector, such as, for example, a connector 60. In some embodiments, spinal correction system 20 may include one or a plurality of connectors 60 spaced apart and disposed along one or a plurality of spinal rods 58. Connector 60 includes a first inner surface that defines a passageway 64 configured for disposal of spinal construct 21. Passageway 64 facilitates movement of the components of spinal construct 21 therealong. Connector 60 includes an inner surface that defines a passageway 66 disposed in a transverse orientation relative to passageway 64. Passageway 66 is configured for disposal of spinal rod 58 such that connector 60 can be mounted with spinal rod 58.

In assembly, operation and use, a surgical system, including spinal correction system 20, similar to the systems and methods described herein, is employed with a surgical procedure, such as, for example, a correction treatment to treat adolescent idiopathic scoliosis and/or Scheuermann's kyphosis of a spine. In some embodiments, one or all of the components of spinal correction system 20 can be delivered or implanted as a pre-assembled device or can be assembled in situ. The system including spinal correction system 20 may be completely or partially revised, removed or replaced.

Figure 14:
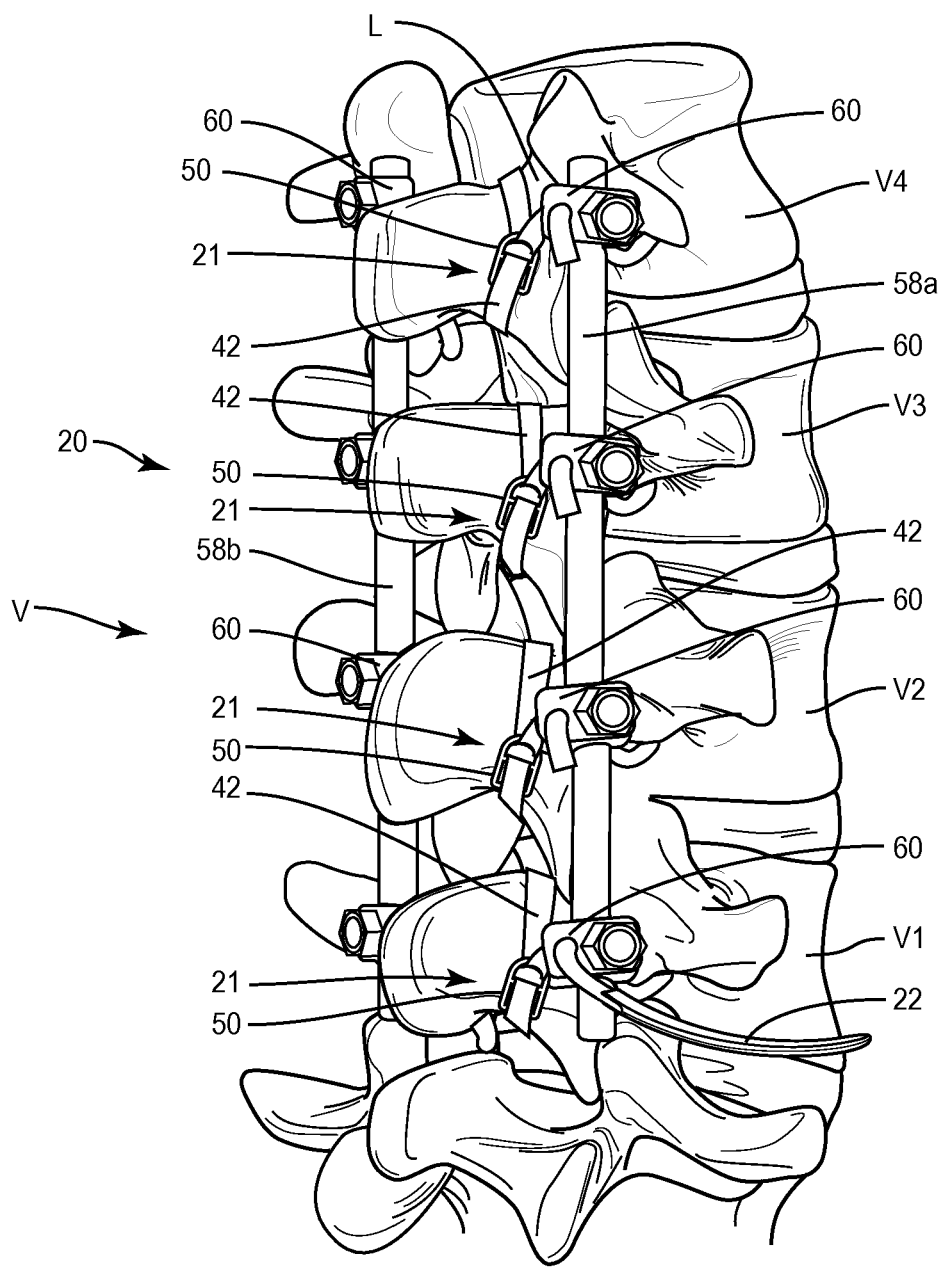
FIG. 14 is a perspective view of components of one embodiment of a spinal correction system in accordance with the principles of the present disclosure disposed with vertebrae.

For example, as shown in FIG. 14, spinal correction system 20 can be employed with a surgical correction treatment of an applicable condition or injury of an affected section of a spinal column and adjacent areas within a body, such as, for example, vertebrae V1-V4 of vertebrae V. In some embodiments, spinal correction system 20 may be employed with one or a plurality of vertebrae.

In use, to treat a selected section of vertebrae V, which includes vertebrae V1-V4, a medical practitioner obtains access to a surgical site including vertebrae V in any appropriate manner, such as through incision and retraction of tissues. In some embodiments, spinal correction system 20 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 20. A preparation instrument (not shown) can be employed to prepare tissue surfaces of vertebrae V, as well as for aspiration and irrigation of a surgical region.

A plurality of spinal constructs 21 are delivered along the surgical pathway to a surgical site adjacent each of vertebrae V1-V4. A practitioner manipulates each spinal construct 21 for disposal about each of vertebrae V1-V4 to fix and/or attach tether 42 with a transverse process and/or a lamina L of each of vertebrae V1-V4, as described above with regard to FIGS. 6-13.

A lead 22 of each spinal construct 21 is guided through the sub-laminar cavity to resist and/or prevent non-desirable and/or harmful engagement with laminae L of each vertebrae V1-V4 and/or dura matter D and without adhering to dura matter D and/or surfaces of laminae L. Lead 22 is drawn or tensioned to adjustably tighten tether 42 with buckle 50 and to fix tether 42 with laminae L of vertebrae V1-V4, as shown in FIG. 14.

A first spinal rod 58*a* is disposed with a connector 60. In some embodiments, connector 60 and spinal rod 58*a* can be delivered or implanted as pre-assembled components or can be assembled in situ. Connector 60 and spinal rod 58*a* are delivered along the surgical pathway to the surgical site adjacent vertebra V4 along a first side of the spinous process. Tether 42, fixed with lamina L of vertebra V4, is slidably drawn or threaded through passageway 64 to dispose connector 60 and spinal rod 58*a* at the surgical site and in contact with vertebra V4.

Spinal correction system 20 includes a plurality of connectors 60 spaced apart along spinal rod 58*a*. Each connector 60 is delivered along the surgical pathway to the surgical site adjacent vertebrae V3-V1 along the first side of the spinous process. Each tether 42, fixed with lamina L of each vertebra V3-V1, is slidably drawn or threaded through passageway 64 to dispose connector 60 and spinal rod 58*a* at the surgical site and in contact with vertebrae V3-V1. In some embodiments, coupling members, such as, for example, set screws secure spinal rod 58*a* and spinal constructs 21 with connectors 60 to attach the implant components of spinal correction system 20 with vertebrae V. In some embodiments, leads 22 are removable from tethers 42 upon disposal of spinal rods 58 and connectors 60 adjacent vertebrae V.

Spinal correction system 20 includes a second spinal rod 58*b* mounted with a plurality of connectors 60 and spinal constructs 21 along a second side of the spinous process. Spinal rods 58*a, b* are mounted with vertebrae V in a side by side orientation. As such, spinal correction system 20 stabilizes vertebrae V and affects growth for a correction treatment to treat various spine pathologies.

Figure 15:
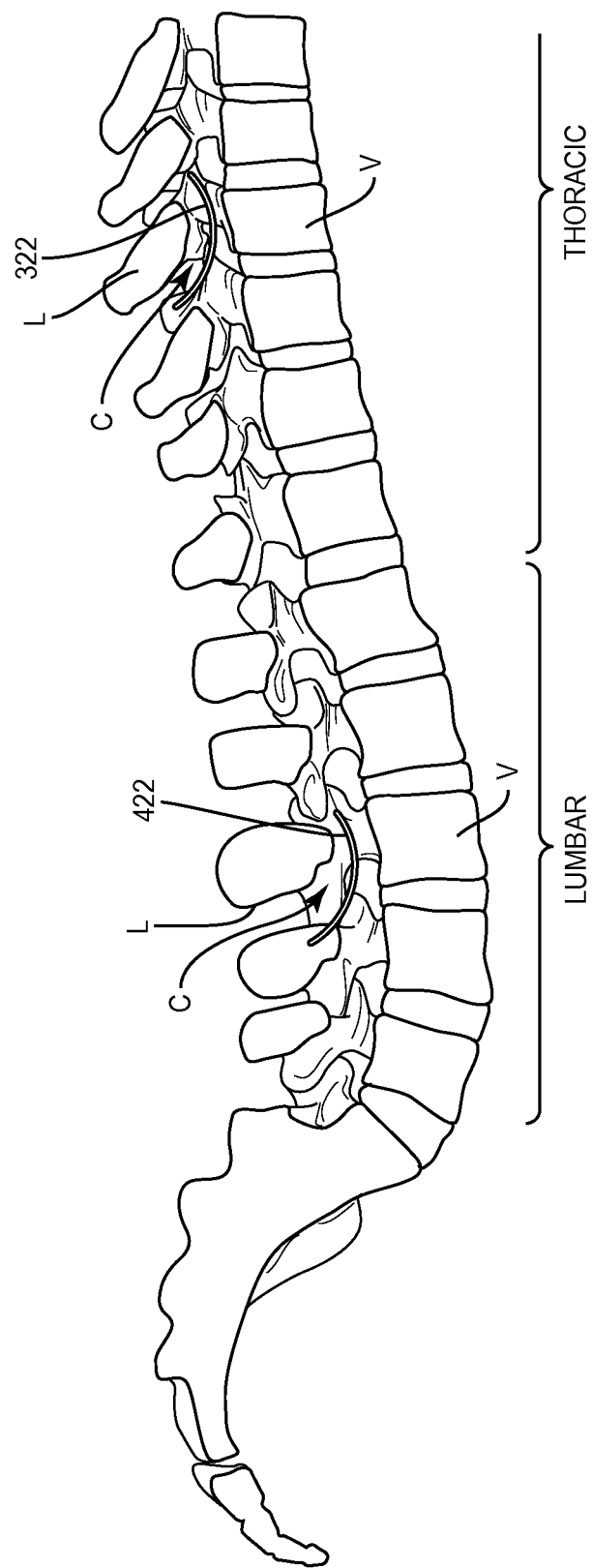
FIG. 15 is a perspective view of components of one embodiment of a spinal correction system in accordance with the principles of the present disclosure disposed with vertebrae.

In one embodiment, as shown in FIG. 15, the targeted section of the spine includes tissue, such as, for example, a lamina L and a sub-laminar cavity C of a vertebra V of a thoracic region of the spine such that spinal construct 21, described herein, includes a lead 322 having a radius of curvature of approximately 80 mm is selected for connection to tether 42, as described herein. In some embodiments, the targeted section of the spine includes tissue, such as, for example, a lamina L and a sub-laminar cavity C of a vertebra V of a lumbar region of the spine such that spinal construct 21, described herein, includes a lead 422 having a radius of curvature of approximately 30 mm is selected.

Upon completion of the procedure, the surgical instruments, assemblies and non-implanted components of spinal correction system 20 are removed and the incision is closed. Spinal correction system 20 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 20. In some embodiments, spinal correction system 20 may include one or a plurality of plates, connectors, spinal rods and/or bone fasteners for use with a single vertebral level or a plurality of vertebral levels.

In some embodiments, the components of spinal correction system 20 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 20 may be used to prevent or minimize curve progression in individuals of various ages.

In one embodiment, spinal correction system 20 includes an agent, which may be disposed, packed, coated or layered within, on or about the components and/or surfaces of spinal correction system 20. In some embodiments, the agent may include bone growth promoting material, such as, for example, bone graft to enhance fixation of the components and/or surfaces of spinal correction system 20 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
    a pliable lead having a paddle configuration including a blunt tip and an inner surface defining a cavity, the lead being concavely curved between the blunt tip and an opposite end surface of the lead; and
    a longitudinal member being flexible relative to the lead, the longitudinal member extending between a first end that is disposed in the cavity and a second end including a buckle that defines an opening configured for movement of the lead therethrough and disposal of the longitudinal member such that the longitudinal member is disposed about spinal tissue.

2. A spinal construct as recited in claim 1, wherein the lead includes an outer surface comprising an average surface roughness in a range of approximately 4 to 16 micro inches.

3. A spinal construct as recited in claim 1, wherein the lead includes an outer surface comprising an average surface roughness configured to resist adherence to a dura of the spinal tissue.

4. A spinal construct as recited in claim 1, wherein the lead is fabricated from a material having a durometer in a range of approximately 30 A to 60 A under the ASTM D2240 type A scale.

5. A spinal construct as recited in claim 1, wherein the lead has a radius of curvature in a range of approximately 20-100 millimeters.

6. A spinal construct as recited in claim 1, wherein the lead has a substantially uniform thickness.

7. A spinal construct as recited in claim 1, wherein the lead is fabricated from silicone.

8. A spinal construct as recited in claim 1, wherein the lead is fabricated from silicone and the longitudinal member includes a tether that comprises at least one of polyester and polyethylene.

9. A spinal construct as recited in claim 1, wherein the buckle is separate and attachable with the longitudinal member.

10. A spinal construct as recited in claim 1, wherein the buckle further comprises a first aperture that is spaced apart from the opening and a second aperture that is spaced apart from the opening and the first aperture.

11. A spinal construct comprising:
    a pliable lead having a paddle configuration including a blunt tip and the lead further comprises an outer surface configured to resist adherence to a dura of spinal tissue and an inner surface defining an elongated cavity, the lead being concavely curved between the blunt tip and an opposite end surface of the lead; and
    a tether being flexible relative to the lead, the tether extending between a first end disposed with the elongated cavity and a second end including a buckle that defines an opening configured for movement of the lead therethrough,
    wherein the lead is movable through a sub laminar cavity of the spinal tissue such that the tether is disposable about a lamina of the spinal tissue and the tether is adjustable with the buckle to fix the tether with the lamina.

12. A spinal construct as recited in claim 11, wherein the lead is fabricated from silicone.

13. A spinal correction system comprising:
    a plurality of spinal constructs, each spinal construct comprising;
        a pliable lead having a paddle configuration including a blunt tip, and
        a longitudinal member being flexible relative to the lead, the longitudinal member extending between a first end connected to the lead and a second end including a buckle that defines an opening;
    at least one spinal rod; and
    a plurality of connectors, each connector including a first passageway configured for disposal of a spinal construct and a second passageway disposed in a transverse orientation relative to the first passageway, the second passageway being configured for disposal of the spinal rod, wherein the lead is movable through a sub laminar cavity of spinal tissue such that the longitudinal member is disposable about a lamina of the spinal tissue and the longitudinal member is adjustable with the second end to fix the longitudinal member with the lamina.

14. A spinal correction system as recited in claim 13, wherein the lead includes an outer surface comprising an average surface roughness in a range of approximately 4 to 16 micro inches.

15. A spinal correction system as recited in claim 13, wherein the lead is concavely curved between the blunt tip and an opposite end surface of the lead.

16. A spinal correction system as recited in claim 13, wherein the lead is fabricated from silicone.

* * * * *